(12) United States Patent
Malm

(10) Patent No.: US 11,486,794 B2
(45) Date of Patent: Nov. 1, 2022

(54) MEASUREMENT OF FLOW OF VENT GAS WITH COMBUSTIBLES

(71) Applicant: REM Technology Inc., Calgary (CA)

(72) Inventor: Howard Malm, Coquitlam (CA)

(73) Assignee: REM Technology Inc., Calgary (CA)

( * ) Notice: Subject to any disclaimer, the term of this patent is extended or adjusted under 35 U.S.C. 154(b) by 0 days.

(21) Appl. No.: 17/325,890

(22) Filed: May 20, 2021

(65) Prior Publication Data

US 2021/0364389 A1 Nov. 25, 2021

Related U.S. Application Data

(60) Provisional application No. 63/027,765, filed on May 20, 2020.

(51) Int. Cl.
*G01M 15/05* (2006.01)
*G01N 33/00* (2006.01)
*G01N 33/22* (2006.01)

(52) U.S. Cl.
CPC ........ *G01M 15/05* (2013.01); *G01N 33/0036* (2013.01)

(58) Field of Classification Search
CPC .. G01M 15/05; G01N 33/0036; G01N 33/225
See application file for complete search history.

(56) References Cited

U.S. PATENT DOCUMENTS 8,235,029 B2 * 8/2012 Malm ................... F02D 19/023
123/518
9,534,564 B2 * 1/2017 Malm .................. F02M 55/007

FOREIGN PATENT DOCUMENTS

JP 2004204746 A * 7/2004

* cited by examiner

*Primary Examiner* — Herbert K Roberts
*Assistant Examiner* — Anthony W Megna Fuentes

(57) ABSTRACT

The present disclosure describes methods and systems for determining a flow of a combustible portion of vent gas delivered to an engine. The flow rate measurement may be performed by using the engine response to a relatively short (e.g. 1 to 5 s) interruption of the vent gas flow. A cross-correlation between RPM data of the engine and a reference signal corresponding to a state of a valve configured to interrupt the vent gas flow is determined, and a flow rate of the combustible portion of the vent gas delivered to the engine is determined from the maximum value of the cross-correlation.

20 Claims, 11 Drawing Sheets

MEASUREMENT OF FLOW OF VENT GAS WITH COMBUSTIBLES

CROSS-REFERENCE TO RELATED APPLICATIONS

The present application claims priority to U.S. Provisional patent application No. 63/027,765, filed on May 20, 2020, the entire contents of which is incorporated herein for all purposes.

TECHNICAL FIELD

The present disclosure relates to flow rate measurement, and in particular to flow rate measurement of vent gas with combustibles used in internal combustion engines.

BACKGROUND

In many industrial processes vent gases with combustible components are released to the atmosphere. These gases may contain undesired components such as benzene or methane. In the technology described by Malm in U.S. Pat. No. 8,113,181 entitled "Method and Apparatus for Capturing and Controlling Fugitive Gases", U.S. Pat. No. 8,235,029 entitled "Method and Apparatus for Processing Diluted Fugitive Gases", U.S. Pat. No. 8,382,469 entitled "Method and Apparatus for Utilising Fugitive Gases as a Supplementary Fuel Source", U.S. Pat. No. 8,851,054 entitled "Apparatus for Providing Diluted Fugitive Gases as a Fuel to an Engine", U.S. Pat. No. 8,978,627 entitled "Method and Apparatus for Capturing and Controlling Fugitive Gases", and U.S. Pat. No. 9,534,564 entitled "System and Method for Controlling a Flow of Vent Gases to a Natural Gas Engine", the entire contents of which are incorporated herein by reference, vent gases with gaseous combustible components are added to the intake air of an internal combustion engine. This reduces the need for engine fuel and efficiently eliminates these components from the vent gases. In the case of methane, which is a potent greenhouse gas, there is a need to measure the flow rate to determine the benefit of the technology. Flow measurement is done either using a calibrated flow meter or calculation using the pressure drop due to a restriction such as an orifice or valve.

Additional, alternative, and/or improved systems and methods that enable for determining the flow of the combustible portion of vent gas remain highly desirable.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
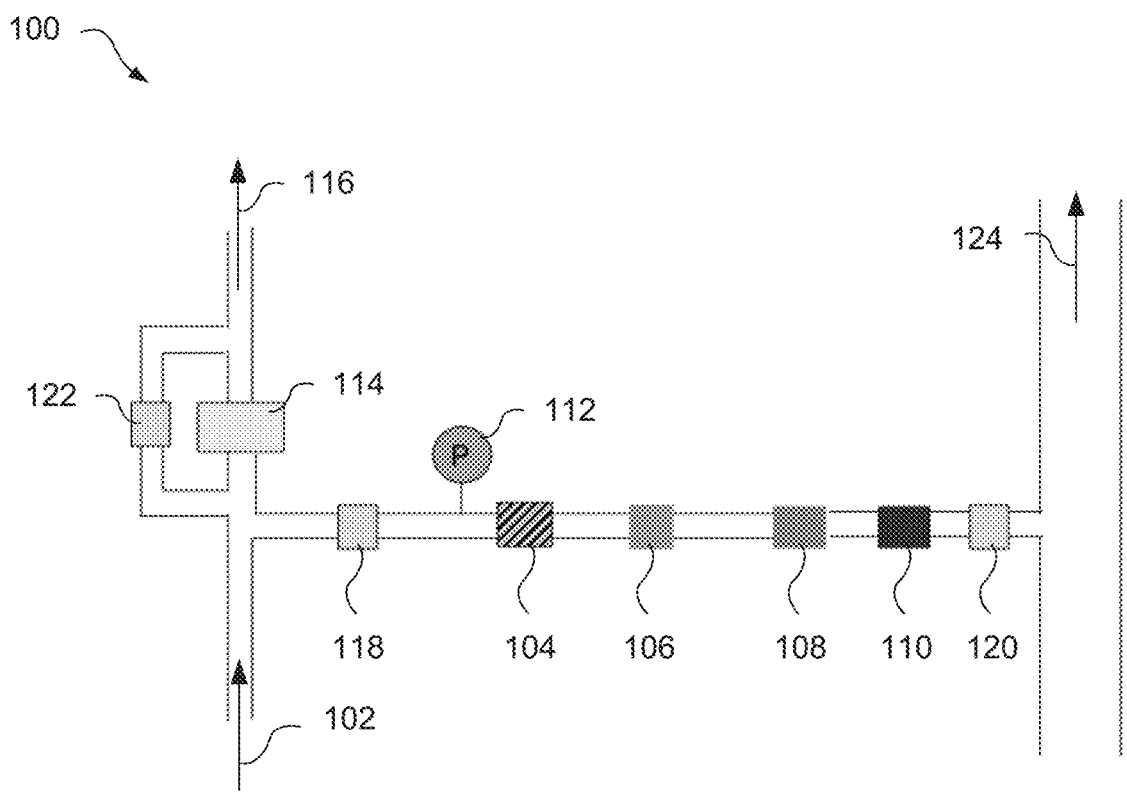
FIG. 1 shows an example representation of a conventional system for controlling non-diluted vent gas flow to engine intake air.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method of determining a flow rate of a combustible portion of vent gas delivered to an engine. The method of determining also includes receiving rpm (revolutions per minute) data of the engine at a sampling rate during a first time period while vent gas is flowing to the engine; after the first time period, controlling a valve to stop flow of the vent gas to the engine for a second time period, and receiving rpm data of the engine during the second time period; upon expiry of the second time period, controlling the valve to resume flow of the vent gas to the engine, and receiving rpm data of the engine during a third time period following the second time period; determining a maximum value of a cross-correlation between the rpm data of the engine and a reference signal corresponding to a state of the valve over a measurement period including the first time period, the second time period, and the third time period, where each of the first, second, and third time periods are equal to or longer than a sampling period corresponding to the sampling rate of the rpm data; and determining the flow rate of the combustible portion of the vent gas delivered to the engine during the first and third time periods from the maximum value of the cross-correlation. Other embodiments of this aspect include corresponding computer systems, apparatus, and computer programs recorded on one or more computer storage devices, each configured to perform the actions of the methods.

One general aspect includes a system for determining a flow rate of a combustible portion of vent gas delivered to an engine. The system also includes a valve configured to permit and stop flow of the vent gas to the engine; an engine sensor configured to generate rpm (revolutions per minute) data of the engine at a sampling rate; and a processor configured to: receive the rpm data from the engine sensor during a first time period while vent gas is flowing to the engine; control the valve to stop the flow of the vent gas to the engine for a second time period after the first time period, and receive rpm data of the engine during the second time period; control the valve to resume the flow of the vent gas to the engine upon expiry of the second time period, and receive rpm data of the engine during a third time period following the second time period; determine a maximum value of a cross-correlation between the rpm data of the engine and a reference signal corresponding to a state of the valve over a measurement period including the first time period, the second time period, and the third time period, where each of the first, second, and third time periods are equal to or greater longer than a sampling period corresponding to the sampling rate of the rpm data; and determine the flow rate of the combustible portion of the vent gas delivered to the engine during the first and third time periods from the maximum value of the cross-correlation. Other embodiments of this aspect include corresponding computer systems, apparatus, and computer programs recorded on one or more computer storage devices, each configured to perform the actions of the methods.

Most internal combustion engines already have instrumentation and electronic control to ensure that the engine operates safely, and emits emissions such as carbon monoxide and nitrogen oxides less than that allowed by regulations. The present disclosure describes a method to measure the flow of a combustible portion of the vent gas by using existing engine instrumentation, thus eliminating the need for a dedicated vent gas flow measurement.

In the technology described by Maim in the above-noted US Patents incorporated herein by reference, the low-pressure vent gases are collected using pipes and added to the engine intake air. To ensure safe operation and release of the gases to the atmosphere when the engine is not running, various valves are used to control the vent gas flow. An example of such an arrangement for vent gases with little or no dilution with non-combustible gases is shown schematically in FIG. 1, which shows an example representation of a conventional system 100 for controlling non-diluted vent gas flow to engine intake air.

Undiluted vent gases indicated by arrow 102 enter the system 100 from one or more sources such as pneumatic devices, petroleum storage tanks, and gas compressor packing leaks. In operation the vent gases flow through a filter 104, an electronic shutoff valve 106, control valve 108, and flow rate sensor 110. The filter 104 serves to remove liquid and solid components. The electronically controlled shut-off valve 106 ensures no vent gases flow to the engine if the engine is not operating or the addition of vent gases to the engine is not desired. A pressure sensor 112 measures the vent gas pressure relative to the atmosphere. The control valve 108 regulates the flow rate of the vent gas 102 to the engine intake. The flow rate sensor 110 measures the vent gas flow rate. If the vent gas flow rate is sufficiently large causing the pressure to exceed a threshold of a pressure relief valve 114, the excess vent gas is released to the atmosphere as indicated by arrow 116. Manual valves such as a manual block and bleed valve 118, manual block valve 120, and manual bypass valve 122 may be provided in the system 100 as a safety measure. The vent gases may be added to the engine intake air, or to the intake manifold if the intake manifold pressure is below atmospheric pressure as with naturally aspirated engines. The intake air to the engine is indicated by arrow 124. By adding the vent gases to the engine intake air, a single vent gas system design is suitable for both naturally aspirated engines and engines using pressurized intake air. An electronic controller, not shown, regulates the control valve 108 using either or both of the pressure sensor 112 and flow rate sensor 110 signals.

Figure 2:
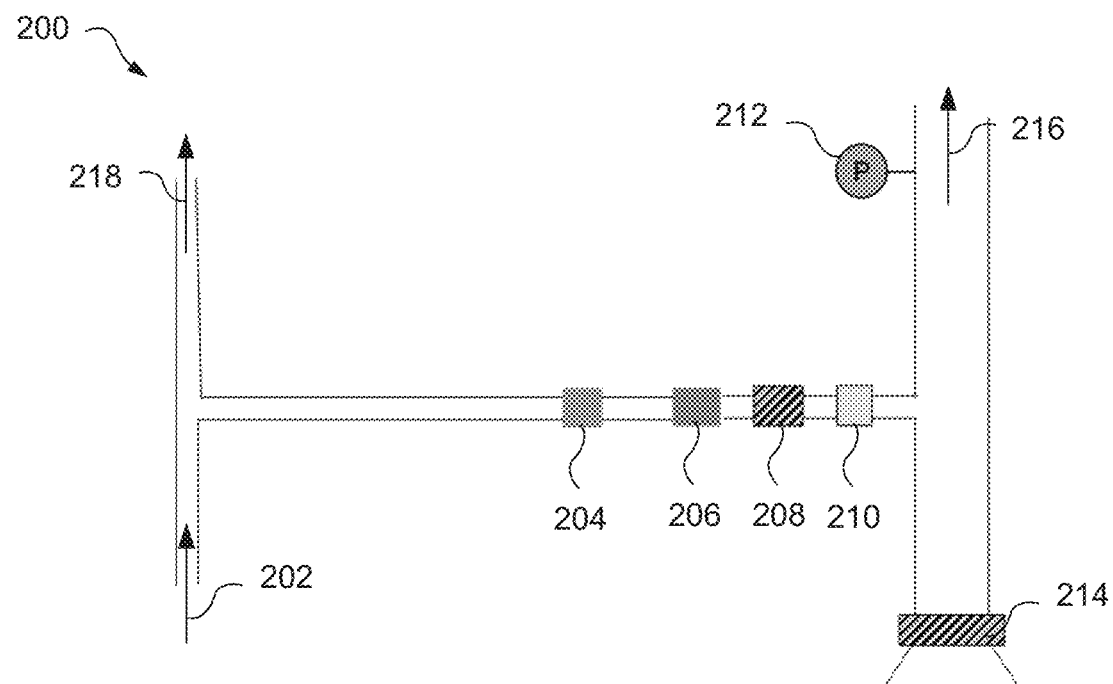
FIG. 2 shows an example representation of a conventional system for controlling diluted vent gas flow to engine intake air.

In another system such as that which is described by Malm in U.S. Pat. No. 8,235,029 for diluted vent gases with combustible components, the combustible portion of the vent gas flow may be measured using the engine RPM change. FIG. 2 shows an example representation of a conventional system 200 for controlling diluted vent gas flow to engine intake air.

Diluted vent gases indicated by arrow 202 enter the system 200. In operation, where an engine intake air filter 214 causes the engine intake air pressure to be less than atmospheric pressure typically by 3 to 15 inches of water column (1 to 4 kilopascals), the vent gases are drawn into the engine intake air, through an electronically controlled shut-off valve 204, control valve 206, and vent gas filter 208, provided the valves 204 and 206 are open. A manual block valve 210 may also be provided. The shutoff valve 204 or the manual block valve 210 can ensure no vent gases reach the engine intake air when the engine is not operating or the addition of vent gases to the engine is not desired. The vent gas filter 208, which may be optional, ensures that no liquid droplets or undesired solid contaminants reach the engine intake air. The intake air to the engine is indicated by arrow 216. A pressure sensor 212 or switch provides a signal of the intake air pressure relative to the atmosphere to an electronic controller (not shown). If, for example, the measured pressure is at or near zero, the electronic controller closes the shut-off valve 204 and the vent gas is vented to atmosphere as indicated by arrow 218. The electronic controller can regulate the vent gas flow rate using the pressure signal.

Figure 3:
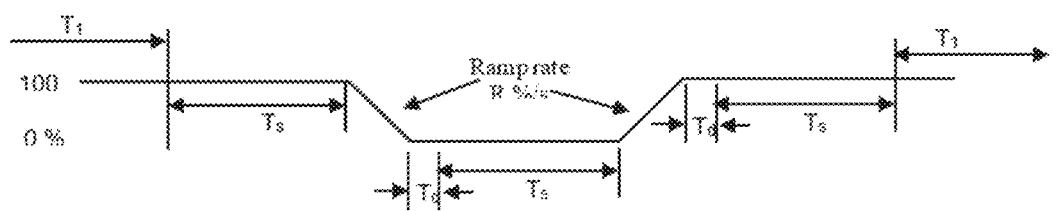
FIG. 3 illustrates engine RPM as a function of various time increments for determining a combustible portion of the diluted vent gas flow in the system of FIG. 2.

Measurement of the vent gas flow rate to the engine intake air may be achieved by observing the change in main engine fuel flow during a stable load period when the vent gas flow is turned off and then on after a suitable delay. Alternately, the fractional change in engine RPM during a stable load period when the vent gas flow is turned off may be measured as shown in FIG. 3. FIG. 3 illustrates engine RPM as a function of various time increments for determining a combustible portion of the diluted vent gas flow in the system of FIG. 2. The change in engine RPM times the main engine fuel flow then provides a value for the combustible portion of the vent gas flow. Compositional gas analyses of the vent gas and the main engine fuel can be used to quantify the flow of individual combustible gases in the vent gases.

However, as previously described, the undiluted vent gas measurement requires dedicated calibrated devices in the vent gas system. For the diluted vent gas measurement, such as with the technique described with reference to FIG. 3, stable engine operation for periods up to a minute is required in order to appropriately measure the change between two values, which restricts the applicability of such a process.

The present disclosure provides an alternate method for determining a flow of vent gas. As described herein, the flow rate measurement may be performed by using the engine response to a relatively short (e.g. 1 to 5 s) interruption of the vent gas flow. A cross-correlation between RPM data of the engine and a reference signal corresponding to a state of a valve configured to interrupt the vent gas flow is determined, and a flow rate of a combustible portion of the vent gas delivered to the engine is determined from the maximum value of the cross-correlation.

Embodiments are described below, by way of example only, with reference to FIGS. 4-16. While the following description is written in relation to natural gas engines, a person skilled in the art will appreciate that the method could be used for any internal combustion engine (e.g. compression ignited/diesel, gasoline), and thus the description with respect to natural gas engines is non-limiting.

Figure 4:
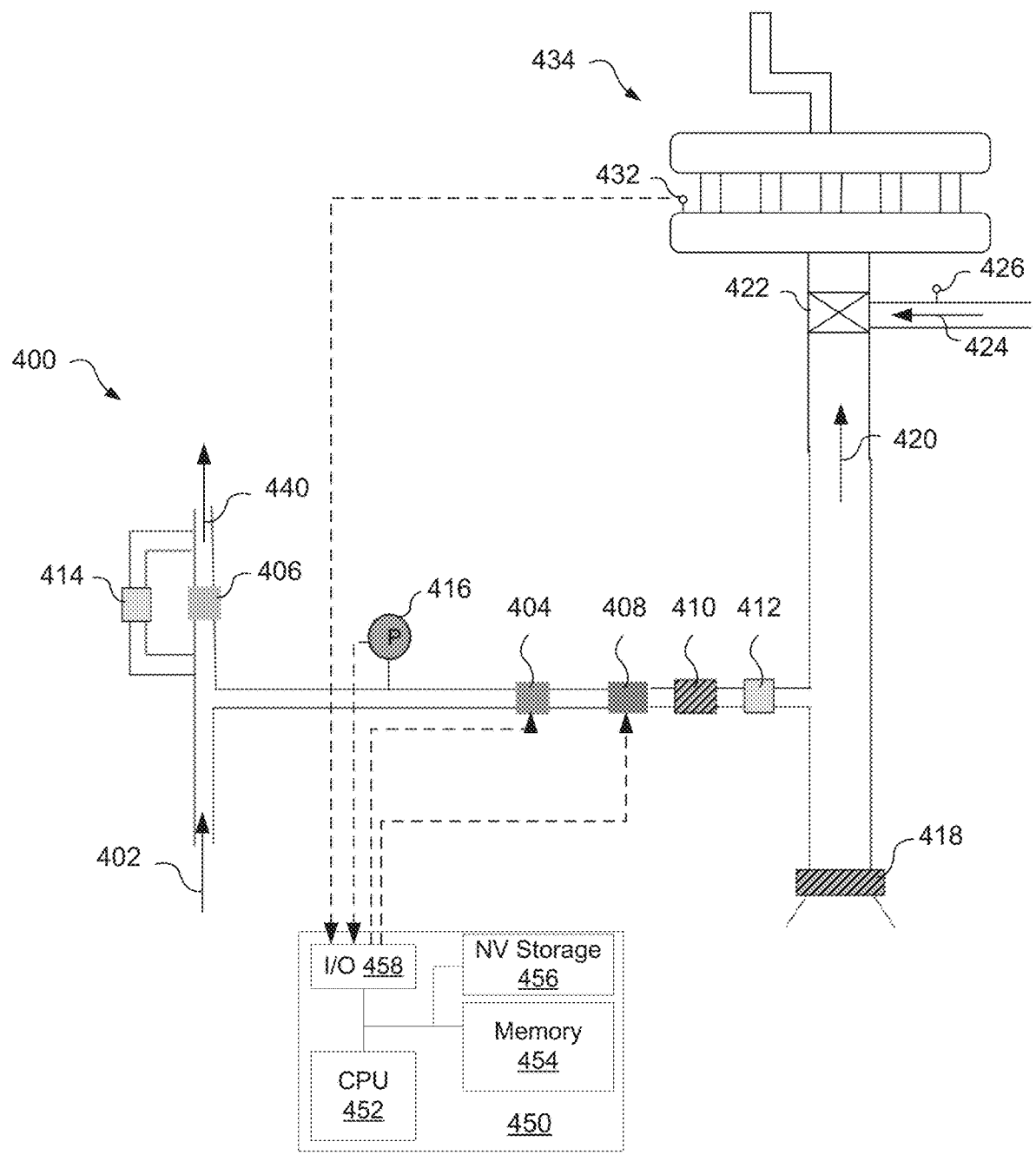
FIG. 4 shows a representation of an example system for controlling and determining non-diluted vent gas flow to engine intake air in accordance with some embodiments of the present disclosure.

FIG. 4 shows a representation of an example system 400 for controlling non-diluted vent gas flow to engine intake air in accordance with some embodiments.

Undiluted vent gases indicated by arrow 402 enter the system 400. A normally closed shut-off valve 404 stops the flow of the vent gas to the intake engine air when de-energized and allows the flow when energized. Intake air to the engine is indicated by arrow 420. When the vent gas flow to the intake air is turned off, or too great for the control valve setting, a pressure relief valve 406 allows the vent gas to flow to the atmosphere as indicated by arrow 440. A control valve 408 controls the vent gas flow rate to the engine intake air as desired. A filter 410 removes foreign material of liquid droplets and solid contaminants from the vent gas flow. Manual valves, such as manual block valve 412 and manual bypass valve 414, may be present to enable system servicing. A pressure sensor 416 measures the pressure of the vent gas relative to the atmospheric pressure. When the engine is operating with an intake air filter 418 in place the intake air pressure is typically in the range of 0.5 to 4 kilopascals below atmospheric pressure.

An electronic controller 450 is configured to control the flow of the vent gas in the system 400. The electronic controller, which is shown in FIG. 4 comprises a central processing unit (CPU) 452, although it may comprise a microprocessor, field programmable gate array (FPGA), or an application specific integrated circuit (ASIC), a non-transitory computer-readable memory 454, a non-volatile storage 456, and an input/output interface 458. The memory 454 stores computer-readable instructions that are executable by the processing unit to configure the electronically to execute certain methods and to provide certain functionality as described herein. The electronic controller 450 is configured to receive data from various sensors and to send control commands to various instrumentation within the system 400 via the I/O interface 458.

To start the vent gas flow to the engine intake air, the electronic controller 450 is configured to cause the shutoff valve 404 to be open (energized) and to cause the control valve 408 to open to govern the vent gas flow rate as desired and to reduce the pressure below the value that causes the relief valve 406 to open and to a desired pressure set-point. The vent gas 402 is added to the engine intake air indicated by arrow 420. The engine intake air is mixed with main fuel indicated by arrow 424 in a mixing chamber 422, and the air-fuel mixture is provided to engine 434.

The electronic controller 450 is also configured to perform a flow measurement. Engine RPM data of engine 434 is collected from an engine sensor 432 at a sampling period corresponding to a sampling rate of several times per second. A few seconds after the start of the RPM sampling, the shut-off valve 404 is closed (de-energized) for a brief period, typically 1 to 5 seconds. The RPM values continue to be collected for a few seconds after the shut-off valve is reopened. If the main fuel flow is measured as shown by fuel flow rate sensor 426, that value may be collected to determine the ratio of vent gas flow to main fuel flow.

Figure 5:
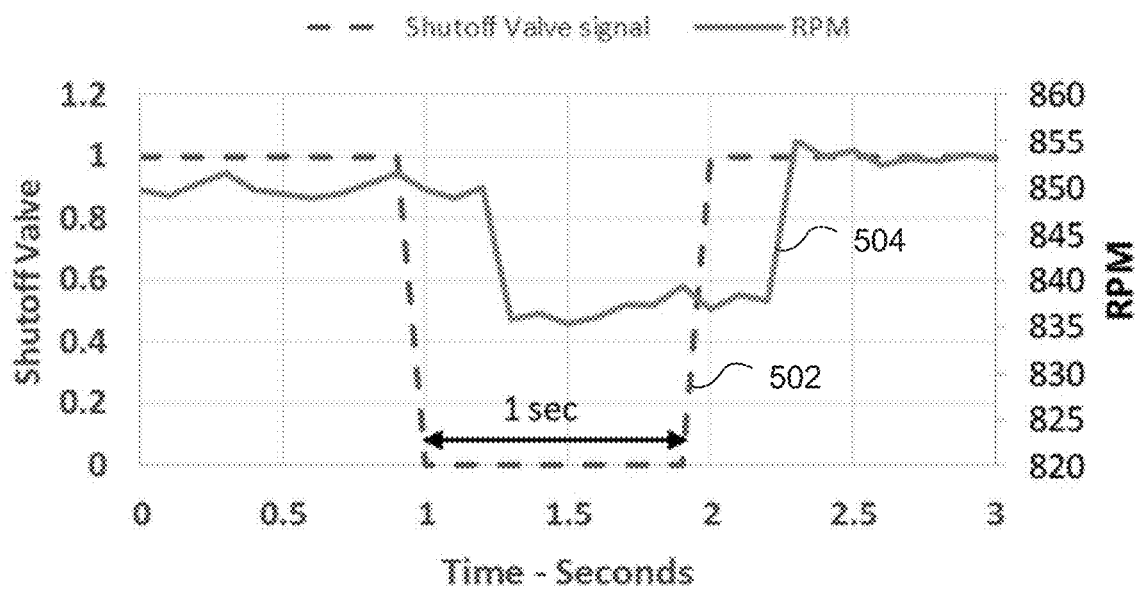
FIG. 5 shows an example of a shut-off valve reference signal and corresponding engine RPM as a function of time obtained via simulation in response to temporarily stopping the non-diluted vent gas flow in the system of FIG. 4.
Figure 6:
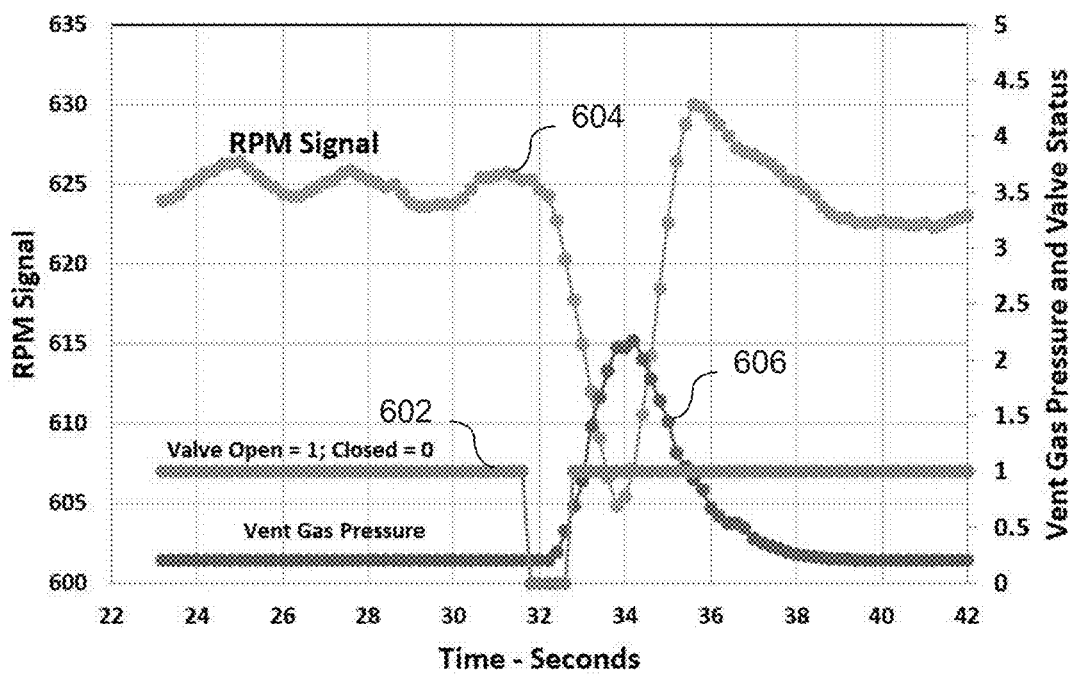
FIG. 6 shows an example of the shut-off valve reference signal and corresponding engine RPM as a function of time obtained via field test results in response to temporarily stopping the non-diluted vent gas flow in the system of FIG. 4.

FIG. 5 shows an example of a shut-off valve reference signal 502 and corresponding engine RPM 504 as a function of time obtained via simulation in response to temporarily stopping the non-diluted vent gas flow (i.e. by closing the shutoff valve 404) in the system of FIG. 4. FIG. 6 shows an example of the shut-off valve reference signal 602 and corresponding engine RPM 604 as a function of time obtained via field test results in response to temporarily stopping the non-diluted vent gas flow in the system of FIG. 4. FIG. 6 further shows vent gas pressure 606 as a function of time. FIG. 6 shows the engine RPM signal 604 recorded every 0.2 s in response to a 1.0 second interruption of the vent gas flow.

During the sampling times depicted in FIGS. 5 and 6, the engine speed is controlled at a set-point by an electronic governor control. After the vent gas flow shutoff valve 404 closes, there is a transit delay before the reduced combustible flow in the vent gas reduces the RPM. The governor control, according to the controller response, adjusts the governor valve to compensate for the temporary reduction in fuel flow. For an engine under a relatively steady load, the RPM temporarily drops, and then recovers as the vent gas shutoff valve 404 is reopened. For an engine driving an AC generator tied to the grid phase, there is a temporary drop in electrical output. In contrast to the simulated RPM signal in response to a 1.0 second vent gas interruption shown in FIG. 5, the field test data in FIG. 6 shows that when the vent gas is turned back on, there is an overshoot of the engine RPM due to the temporarily larger vent gas flow as a result of the build-up of pressure in the vent gas control system during the vent gas flow interruption.

Figure 7:
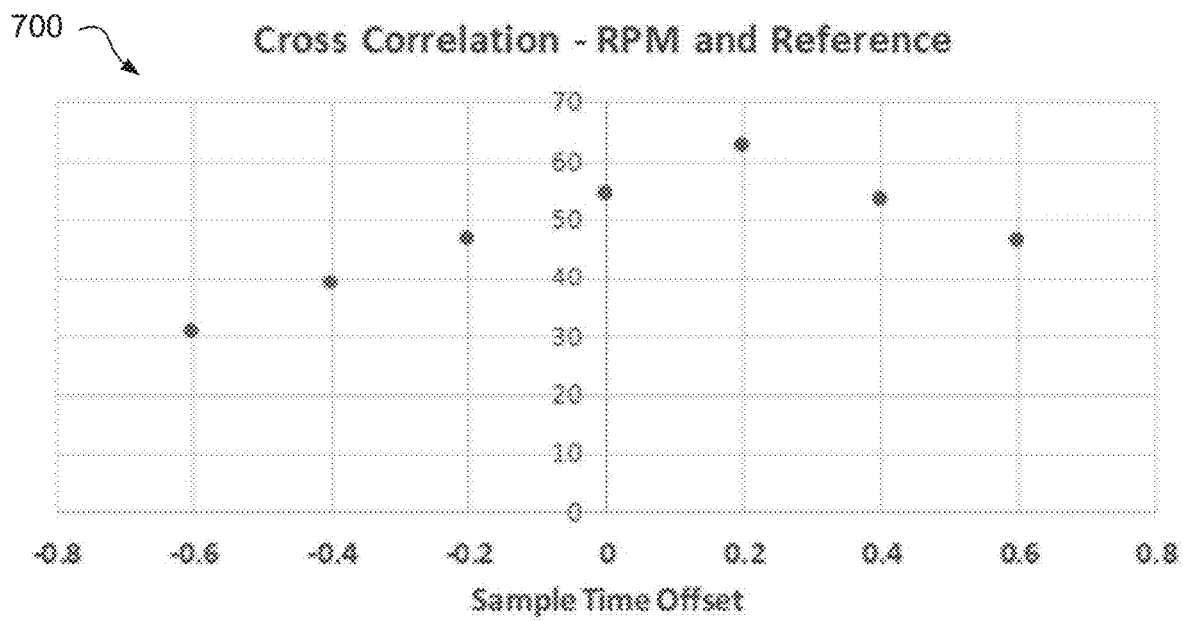
FIG. 7 shows a graph of a cross-correlation of the shutoff valve reference signal and the engine RPM as a function of offset from the graph shown in FIG. 5.

Since the shutoff valve reference signal and the engine RPM or load are correlated, a cross-correlation calculation can be performed using the shutoff valve data as a reference series and the engine RPM data as a sample series. For example, a sample series $x(t_i) \ldots x(t_n)$ is first multiplied by the reference sample series $y(t^i) \ldots y(t_i)$ to form a product $\Sigma x(ti)*y(ti)$ where i goes from i to n; then a second product $\Sigma x(t_{i+1})*y(ti)$ where i goes from i to n is calculated and so on. In effect, one signal is moved past the other. A maximum or minimum is reached when the series are matched. In this case the RPM is the sample series and the shut-off valve signal series serves as the reference. A net change in the maximum change of the cross-correlation value is used. The result of the cross-correlation calculation is proportional to the released energy of the combustible portion of the vent gas, as a larger vent gas flow rate has a greater effect on the engine RPM. FIG. 7 shows a graph 700 of a cross-correlation of the shutoff valve reference signal and the engine RPM as a function of offset from the graph shown in FIG. 5. For this example, the maximum correlation occurs with a time offset of 0.2 s. The offset is due to the transit delay or lag of vent gas to the engine cylinders.

Figure 8:
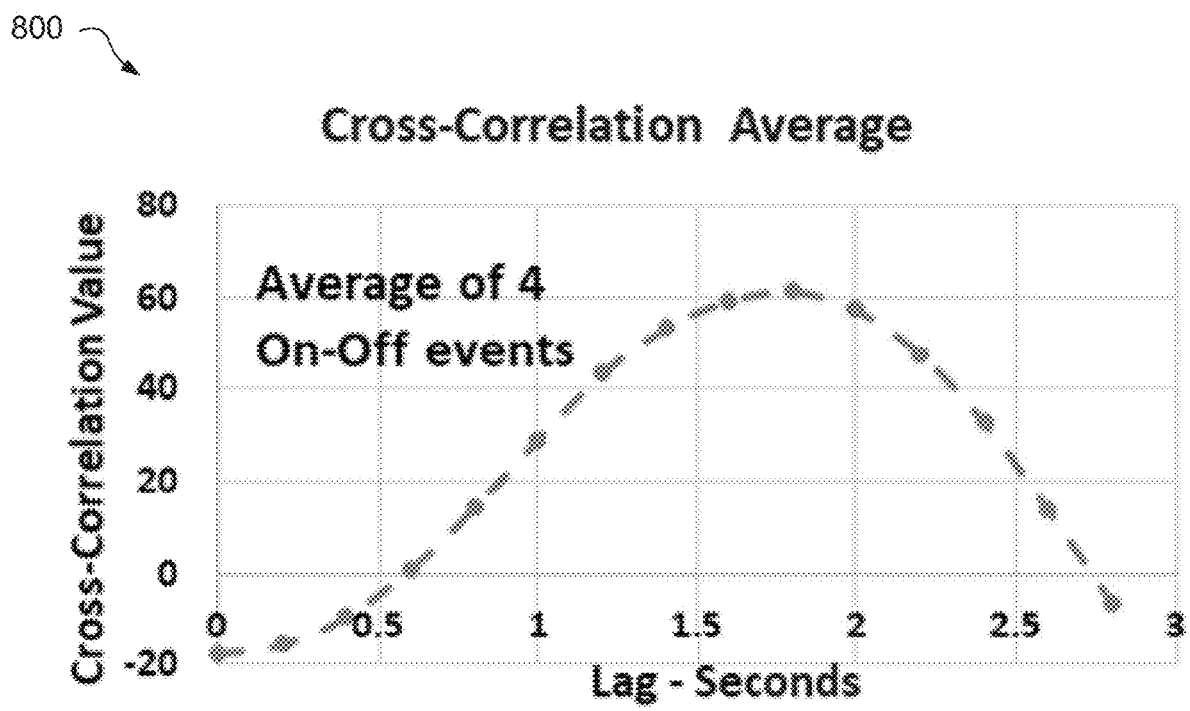
FIG. 8 shows a graph of a cross-correlation of the shutoff valve reference signal and the engine RPM as a function of offset from the graph shown in FIG. 6.

FIG. 8 shows a graph 800 of a cross-correlation of the shutoff valve reference signal and the engine RPM as a function of offset (expressed as lag in seconds) from the graph shown in FIG. 6. The standard deviation of the maximum cross-correlation value of 4 successive events was 2.5% of the average cross-correlation value. Normally, the maximum cross-correlation value may be used, but by performing repeated tests and averaging the resulting maximum cross-correlation value, this reduces the measurement uncertainty particularly for conditions of a relatively small vent gas flow and/or a noisy RPM signal. In this example, the maximum occurs at a lag of 1.8 seconds. Since the maximum cross-correlation value may occur at slightly different lag times, each time a vent gas flow measurement is performed the cross-correlation value may be calculated for a range of lag times and the maximum value selected from those results.

Note that while FIGS. 7 and 8 show a cross-correlation calculating using the shutoff valve reference signal and the engine RPM, one possible improvement is to modify the reference shut-off valve signal, as shown in FIG. 5. To allow for engine-load inertial effects, which causes the engine speed rate of change to be slower than the valve control signal.

Figure 9:
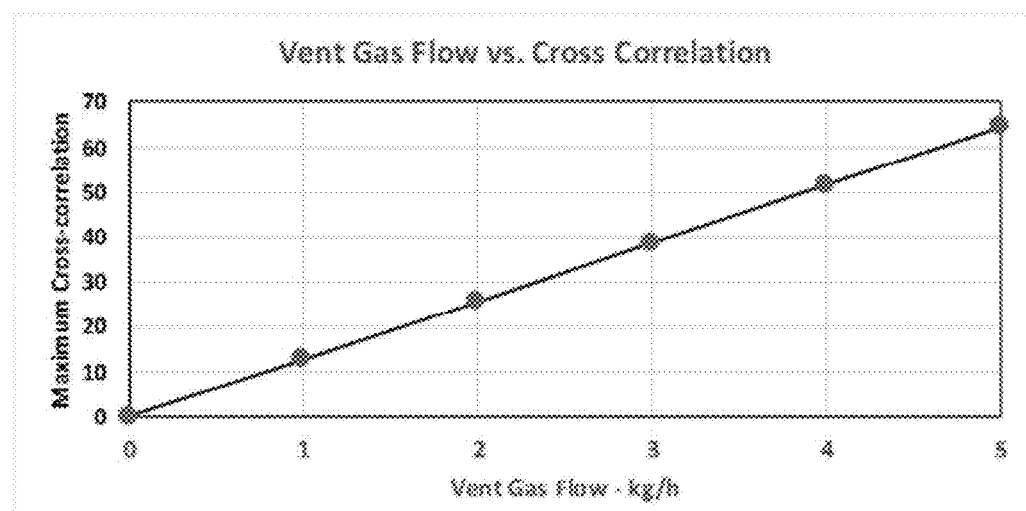
FIG. 9 shows a graph of cross-correlation value vs. vent gas flow obtained from simulation.

The maximum value of the cross-correlation is proportional to the ratio of the released heat of the vent gas combustible component to that of the combustible component of normal engine fuel flow. To convert the cross-correlation value to a vent-gas flow rate requires a conversion factor. This is shown in FIG. 9, which shows a graph 900 of maximum cross-correlation value vs. vent gas flow obtained from a simulation of the engine RPM and a shutoff valve reference function, where the maximum cross-correlation values were calculated for several different flow rates of the vent gas. FIG. 9 shows that a linear relationship between the vent gas flow rate and the maximum of the cross correlation calculation exists.

The conversion factor can also be determined by a test where the vent gas is replaced by a known flow of a combustible calibration gas to determine a conversion factor for the calibration gas. If the vent gas and the combustible gas used for calibration have different compositions, the respective compositions are taken into consideration to relate the conversion factor for the calibration gas to a conversion factor for the vent gas. The released heat per unit flow of the combustion of the vent gas and main fuel can be determined from gas analyses and reference tables of the heat content of the components.

Figure 10:
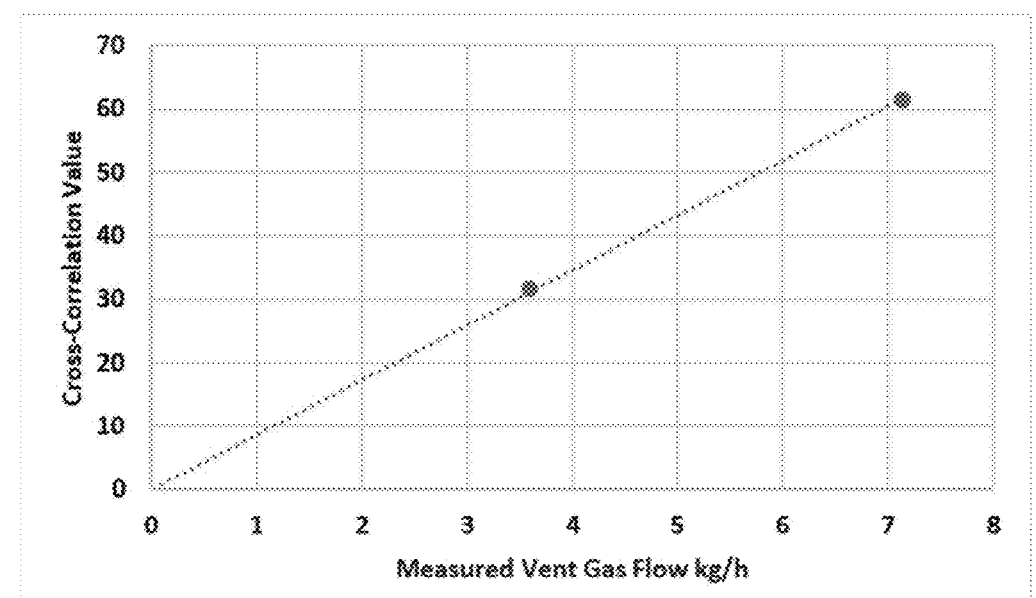
FIG. 10 shows a graph of cross-correlation value vs. measured vent gas flow.

The conversion factor can also be determined by temporarily placing a calibrated flow meter in the vent gas line and comparing the cross-correlation value to the measured vent gas flow rate as is shown in FIG. 10, which shows a graph 1000 of cross-correlation value vs. measured vent gas flow.

Alternatively, the flow rate through a calibrated orifice under critical flow conditions can be used if the supply pressure upstream of the orifice is known. The supply gas pressure may be determined by a pressure regulator set to a known pressure or measured with a pressure sensor. If the ratio of the absolute upstream gas pressure to the absolute downstream gas pressure exceeds the choked flow ratio, the flow rate through the orifice depends primarily on the upstream pressure and weakly on the temperature. For natural gas the choked flow ratio is 1/0.54=1.85. For a downstream pressure in a system of 110 kPa(a), the upstream pressure must exceed 203 kPa(a) or 113 kPa(g) (16 PSIG), assuming an atmospheric pressure of 90 kPa(a) (13 psia). Under critical flow conditions the upstream absolute pressure must exceed the downstream absolute pressure by an approximate factor of >1.9 for any gas that has 2 or more atoms per molecule. With critical flow, changes to the downstream pressure do not affect the flow rate. Flows may be calculated for choked flow conditions using the following formula (1):

$$F=4.726\times10^{-7}*P*d^2/(MW*(T+273))^{0.5} \quad (1),$$

where F is the flow in m³/h, P is the absolute upstream absolute pressure in kPa(a), d is the orifice diameter in microns, MW is the gas molecular wt., and T is the gas temperature in degrees C.

FIGS. 11 to 14 show graphs showing how changes in gas pressure, temperature, and molecular weight affect choked vent gas flow. In these graphs, the gas was pure methane and the orifice diameter equaled 1000 microns=1 mm.

Figure 11:
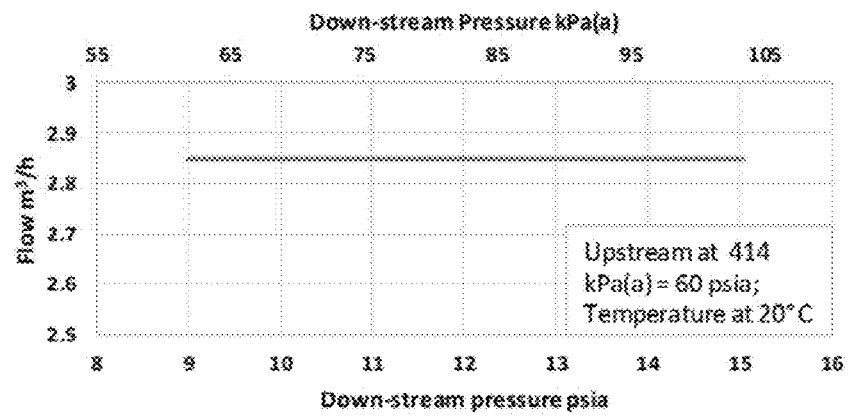
FIGS. 11 to 14 show graphs showing how changes in gas pressure, temperature, and molecular weight affect choked vent gas flow.

FIG. 11 shows a graph 1100 showing that changes in the downstream pressure have no effect on the flow rate for a fixed temperature and upstream pressure. While the expansion of the gas from the high-pressure side of the orifice produces some cooling, it can also be shown that this cooling has negligible effect on the flow rate through the orifice.

Figure 12:
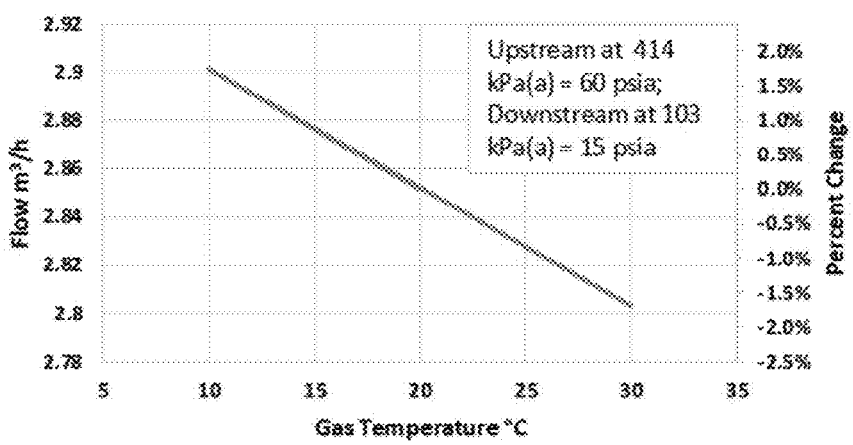

FIG. 12 shows a graph 1200 showing that the gas temperature has a relatively small effect on the standard flow rate. A 10 degrees C. change in the upstream gas temperature affects the flow rate by about 1.3%.

Figure 13:
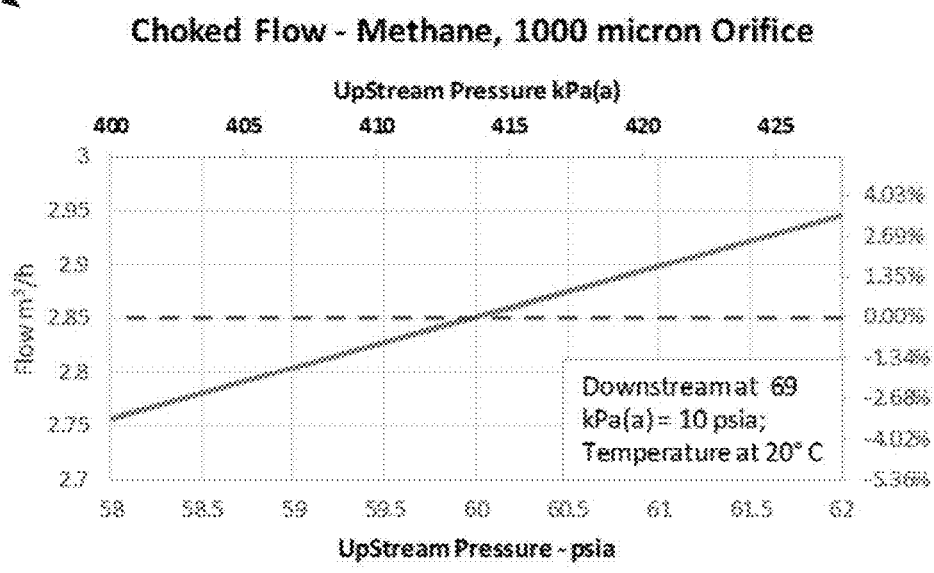

FIG. 13 shows a graph 1300 taken at 20 degrees C. showing that the largest effect is the upstream pressure. A change in the upstream pressure by 2 psi (14 kPa) changes the flow by about 4%.

Figure 14:
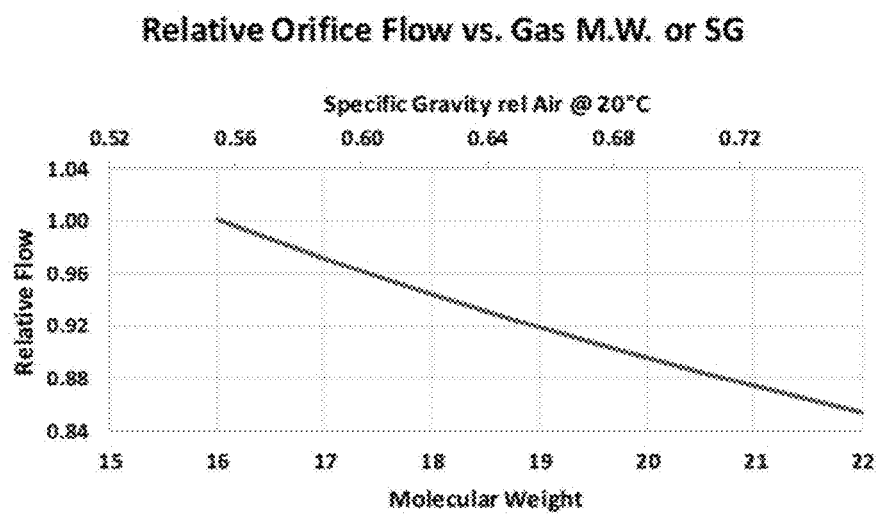

FIG. 14 shows a graph 1400 showing that the gas molecular weight or specific gravity also has an effect as shown.

Various calibration set-ups are possible for determining the flow rate of the vent gas using a calibrated orifice.

For example, a portable arrangement may comprise a calibration gas line from a higher pressure source, such as a gas bottle of pressurized methane, and comprising a pressure regulator, an absolute pressure gas gauge covering the range to 200 kPa(a), a shut-off valve, and a calibrated orifice of known size, that is configured to be connected to the system downstream of the vent gas shut-off valve. A temperature gauge could also be provided. With reference to FIG. 4, the calibration gas line may be connected directly to the intake air duct between the filter 418 and mixing chamber 422.

The user would cause the vent gas shutoff valve 404 to close, open the calibration gas line shutoff valve, and set the calibrated orifice to a fixed open percentage. Then the pressurized methane source would be turned on and the pressure adjusted to the pre-set desired value. This would then provide a known flow rate of the calibration gas, which can be used to determine a conversion factor for the calibration gas. A calibration period of 10 to 15 minutes should be sufficient. While the preferred gas would be 99+% methane, the gas could also be dry air.

In another arrangement, a fixed in-place manual system may comprise a pressurized gas source, for example the engine fuel gas or the compressor gas, along with a pressure regulator, pressure gauge, a shut-off valve, a calibrated orifice, and as an option a temperature gauge, that is connected to the system downstream of the vent gas shutoff valve 404 and may be connected directly to the intake air duct between the filter 418 and mixing chamber 422.

The user would cause the vent gas shutoff valve 404 to close, open the calibration gas line shutoff valve, and set the calibrated orifice to a fixed open percentage. Then the gas source would be turned on and the pressure adjusted to the pre-set desired value. This would then provide a known flow rate of the calibration gas, which can be used to determine a conversion factor for the calibration gas. Based on a composition analysis of the calibration gas and the vent gas, an adjustment factor between the conversion factor for the calibration gas and the conversion factor for the vent gas may be determined. For example this may be determined by the square-root of the ratio of the gas densities applied to the gas flow rate. A calibration period of 10 to 15 minutes should be sufficient.

As a further arrangement, a fixed automatic calibration could be provided that is similar to the fixed manual system except that a calibration solenoid would replace the manual shut-off valve and a pressure transmitter and optional temperature transmitter would replace the dial gauges. A software module may reside in the controller (e.g. controller 450) to perform the calibration function at the desired interval. The source gas could be either the engine fuel gas or a side-stream from the compressor gas.

An arrangement using a calibrated orifice would thus enable the conversion factor for the cross-correlation calculation to flow rate to be determined, and this determination could be automated, allowing a controller such as the controller 450 to schedule a calibration event on a daily or weekly basis, for example.

In summary, based on a maximum value of a cross-correlation as described above, and a known conversion factor for converting the maximum value of the cross-correlation to a flow rate of the vent gas, the flow rate of the vent gas can be determined. Therefore, the vent gas flow rate can be accurately determined by a simple and short interruption of the vent gas flow to the intake engine air. The measurement can be repeated as required either to improve accuracy or to track changes in the vent gas flow rate.

While the vent gas flow is stopped by closing the vent gas shutoff valve, it may be vented to the atmosphere. The vented fraction is relatively small. For example, with a shutoff period of 1 second and a flow test every 15 minutes, the maximum fraction of vent gas that can be released to the atmosphere is 0.11%. If it is desired to completely eliminate the release to the atmosphere, a volume accumulator such as described by Maim in U.S. Pat. No. 8,113,181, may be attached to the vent gas piping before the shut-off valve to absorb the vent gas during the shutoff period.

There are a number of further embodiments possible. One such embodiment is by modelling the reference RPM response function to match the expected governor response to fuel flow changes. Another possible improvement is performing repeated tests and averaging the resulting maximum cross-correlation value. This reduces the measurement uncertainty for conditions of a relatively small vent gas flow and a noisy RPM signal.

The flow rate of methane in the vent gas flow may be determined from the component analysis of the vent gas. This can be used to quantify the reduction of methane release to the atmosphere if not combusted in the engine.

Figure 15:
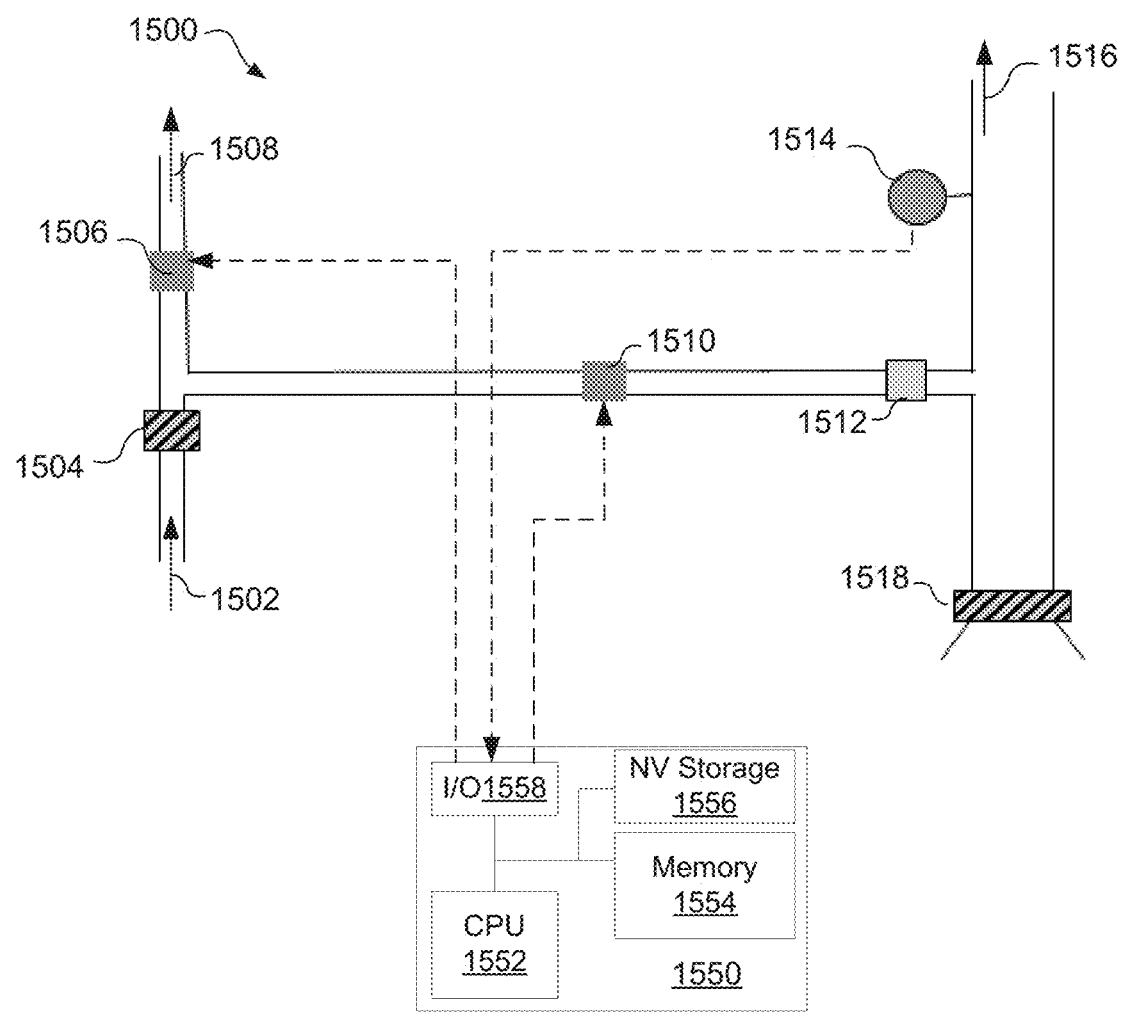
FIG. 15 shows a representation of an example system for controlling and determining diluted vent gas flow to engine intake air in accordance with some embodiments.

For diluted vent gases the cross-correlation measurement method described in the foregoing description may also be used. FIG. 15 shows a representation of an example system for controlling and determining diluted vent gas flow to engine intake air in accordance with some embodiments. The system 1500 shown in FIG. 15 is suitable for crankcase vent gas from a natural gas engine. Such crankcase gas contains methane from the methane component in the engine fuel as documented by Johnson et. al. ("Methane Emissions from Leak and Loss Audits of Natural Gas Compressor Stations and Storage Facilities" Environ. Sci. Technol., 2015, 49 (13), pp 8132-8138) and Clark et. al. ("Pump-to-Wheels Methane Emissions from the Heavy-Duty Transportation Sector" Environ. Sci. Technol. 2017, 51, 968-976"), the entire contents of which are incorporated herein by reference. Other arrangements may be used according to the properties of the vent source and the vent gases.

Diluted vent gases indicated by arrow 1502 enter the system 1500. A filter 1504 ensures that any foreign materials or liquid droplets are removed from the vent gas. A shutoff valve 1506, which may be normally open, allows the vent gases to flow to the atmosphere, as indicated by arrow 1508, when the engine is either not operating or the valves including a shutoff valve 1510, which may be normally closed, and a manual block valve 1512 allowing flow to the engine intake are closed. A pressure switch 1514 checks for a negative pressure for the intake air flowing to the engine, which is indicated by arrow 1516. The engine and associated intake lines and mixing chamber is not shown in FIG. 15 but has previously described with reference to FIG. 4.

When the engine is operating with an intake air filter 1518 in place, the intake air pressure is typically in the range of 0.5 to 4 kilopascals below atmospheric pressure. In operation, when the pressure switch 1514 indicates a negative pressure of the intake air, a controller 1550, which may be similar to controller 450 as previously described, energizes the normally-closed shutoff valve 1510 to open and the normally-open shutoff valve 1506 is energized to close. This allows the diluted vent source gas to flow to the engine air intake.

To perform a measurement of the combustible component of the vent gas, both shutoff valves 1506 and 1510 are controlled to temporarily interrupt the flow to the engine and allow flow to the atmosphere.

An example of a correlation between a shutoff valve reference signal and the engine RPM has been previously described with reference to FIGS. 5 and 6. The maximum cross-correlation between a reference signal and the engine RPM is proportional to the combustible component flow. The measurement may be repeated as determined by the need for reduced uncertainty or regulation. The methane component can be determined from a component analysis of the crankcase gases.

Other arrangements of the apparatus for directing vent gases to the engine intake air can be used. For naturally aspirated engines with intake manifold pressures less than atmospheric pressure, the vent gases can be directed directly to the intake manifold.

More than one vent gas sources may be used. If required, the combustible component flow from each source may be determined using this measurement process.

Figure 16:
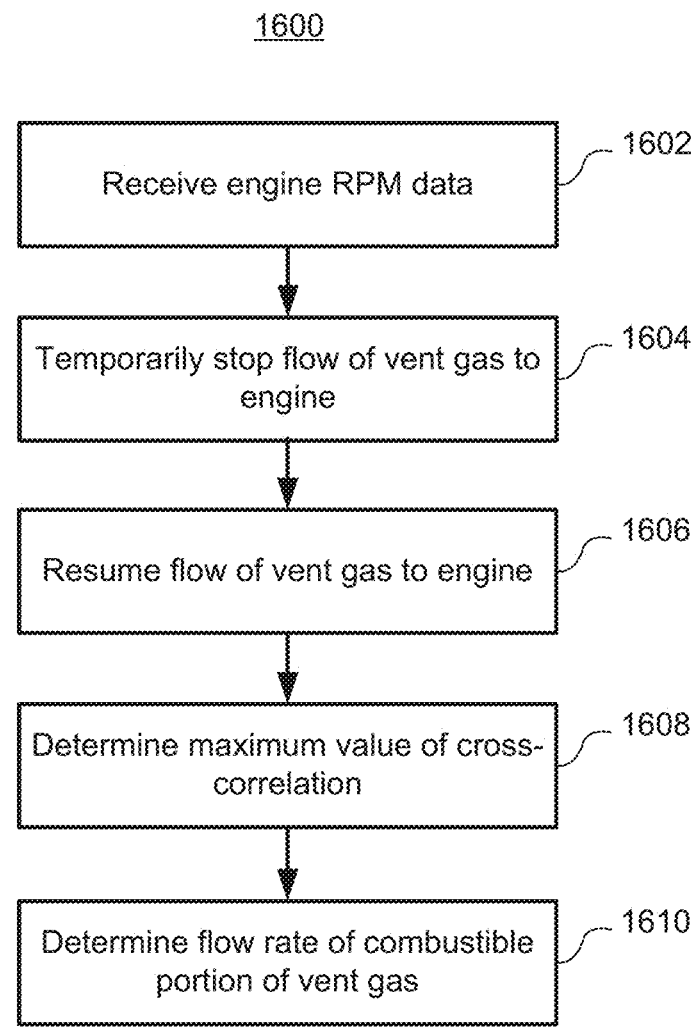
FIG. 16 shows a method of determining a flow rate of a combustible portion of vent gas delivered to an engine.

FIG. 16 shows a method 1600 of determining a flow rate of a combustible portion of vent gas delivered to an engine. The method 1600 may be performed by the controller 450 and/or 1550. The method 1600 comprises receiving RPM (revolutions per minute) data of the engine at a sampling rate during a first time period while vent gas is flowing to the engine (1602). After the first time period, one or more valves are controlled to temporarily stop flow of the vent gas to the engine for a second time period, and RPM data of the engine is received during the second time period (1604). For example, the second time period may be between 1 and 5 seconds. Upon expiry of the second time period, the valve(s) is/are controlled to resume flow of the vent gas to the engine, and RPM data of the engine is received during a third time period following the second time period (1606). A determination of a maximum value of a cross-correlation between the RPM data of the engine and a reference signal corresponding to a state of the valve is made (1608), the cross-correlation being performed over a measurement period comprising the first time period, the second time period, and the third time period, wherein each of the first, second, and third time periods are equal to or longer than the sampling rate of the RPM data. As described above, the time of interrupted flow corresponding to the second time period can be kept short, and may be between one and five seconds. The first and third time periods may be equal to or longer than the second time period, and the first and third time periods do not necessarily have to be the same. The flow rate of the combustible portion of the vent gas delivered to the engine during the first and third time periods is determined from the maximum value of the cross-correlation (1610). Specifically, as described above, the maximum value of the cross-correlation is proportional to a ratio of heat released from the vent gas combustible component to heat released from the combustible component of normal engine fuel flow. The conversion factor can be determined by a test where the vent gas is replaced by a flow of a known combustible gas and/or by the use of a calibrated orifice. The conversion factor can also be determined by temporarily placing a calibrated flow meter in the vent gas line and comparing the cross-correlation value to the measured vent gas flow rate. The released heat per unit flow of the combustion of the vent gas and main fuel can be determined from gas analyses and reference tables of the heat content of the components.

It would be appreciated by one of ordinary skill in the art that the system and components shown in the Figures may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as described herein.

The invention claimed is:

1. A method of determining a flow rate of a combustible portion of vent gas delivered to an engine, comprising: receiving RPM (revolutions per minute) data of the engine at a sampling rate during a first time period while vent gas is flowing to the engine; after the first time period, controlling a valve to stop flow of the vent gas to the engine for a second time period, and receiving RPM data of the engine during the second time period; upon expiry of the second time period, controlling the valve to resume flow of the vent gas to the engine, and receiving RPM data of the engine during a third time period following the second time period; determining a maximum value of a cross-correlation between the RPM data of the engine and a reference signal corresponding to a state of the valve over a measurement period comprising the first time period, the second time period, and the third time period; wherein each of the first, second, and third time periods are equal to or longer than a sampling period corresponding to the sampling rate of the RPM data; and determining the flow rate of the combustible portion of the vent gas delivered to the engine during the first and third time periods from the maximum value of the cross-correlation.

2. The method of claim 1, wherein the first and third time periods are equal to or greater than the second time period.

3. The method of claim 1, wherein the second time period is between one and five seconds.

4. The method of claim 1, wherein determining the maximum value of the cross-correlation between the RPM data of the engine and the reference signal comprises averaging a plurality of maximum values from a plurality of successive tests.

5. The method of claim 1, wherein the maximum value of the cross-correlation is proportional to a ratio of heat released from the combustible component of the vent gas to heat released from a combustible component of engine fuel flow.

6. The method of claim 1, wherein the flow rate of the combustible portion of the vent gas delivered to the engine during the first and third time periods is determined from the maximum value of the cross-correlation using a conversion factor.

7. The method of claim 6, wherein the conversion factor is determined by one or more of: replacing the vent gas with a known flow rate of a calibration gas; using a calibrated orifice to determine a flow rate of a known gas; and using a calibrated flow meter to determine the flow rate of the vent gas.

8. The method of claim 1, further comprising determining a composition of the vent gas, and determining a flow rate of a constituent of the vent gas based on the flow rate of the vent gas and the composition of the vent gas.

9. The method of claim 1, wherein the vent gas is diluted or undiluted.

10. The method of claim 1, wherein the engine is an internal combustion engine.

11. A system for determining a flow rate of a combustible portion of vent gas delivered to an engine, comprising: a valve configured to permit and stop flow of the vent gas to the engine; an engine sensor configured to generate RPM (revolutions per minute) data of the engine at a sampling rate; and a processor configured to: receive the RPM data from the engine sensor during a first time period while vent gas is flowing to the engine; control the valve to stop the flow of the vent gas to the engine for a second time period after the first time period, and receive RPM data of the engine during the second time period; control the valve to resume the flow of the vent gas to the engine upon expiry of the second time period, and receive RPM data of the engine during a third time period following the second time period; determine a maximum value of a cross-correlation between the RPM data of the engine and a reference signal corresponding to a state of the valve over a measurement period comprising the first time period, the second time period, and the third time period; wherein each of the first, second, and third time periods are equal to or greater longer than a sampling period corresponding to the sampling rate of the RPM data; and determine the flow rate of the combustible portion of the vent gas delivered to the engine during the first and third time periods from the maximum value of the cross-correlation.

12. The system of claim 11, wherein the first and third time periods are equal to or greater than the second time period.

13. The system of claim 11, wherein the second time period is between one and five seconds.

14. The system of claim 11, wherein the processor is configured to average a plurality of maximum cross-correlation values to determine the maximum value of the cross-correlation between the RPM data of the engine and the reference signal.

15. The system of claim 11, wherein the maximum value of the cross-correlation is proportional to a ratio of heat released from the combustible component of the vent gas to heat released from a combustible component of engine fuel flow.

16. The system of claim 11, wherein the flow rate of the combustible portion of the vent gas delivered to the engine during the first and third time periods is determined from the maximum value of the cross-correlation using a conversion factor.

17. The system of claim 16, wherein the processor is configured to determine the conversion factor using flow rate data received from:
replacing the vent gas with a known flow rate of a calibration gas; using a calibrated orifice to determine a flow rate of a known gas; and using a calibrated flow meter to determine the flow rate of the vent gas.

18. The system of claim 11, wherein the processor is further configured to determine a composition of the vent gas, and determine a flow rate of a constituent of the vent gas based on the flow rate of the vent gas and the composition of the vent gas.

19. The system of claim 11, wherein the vent gas is diluted or undiluted.

20. The system of claim 11, wherein the engine is an internal combustion engine.

* * * * *